(12) United States Patent
Darwish

(10) Patent No.: US 11,529,113 B2
(45) Date of Patent: Dec. 20, 2022

(54) MAGNETIC CLIP STETHOSCOPE HOLDER

(71) Applicant: Omar Darwish, Tustin, CA (US)

(72) Inventor: Omar Darwish, Tustin, CA (US)

( * ) Notice: Subject to any disclaimer, the term of this patent is extended or adjusted under 35 U.S.C. 154(b) by 796 days.

(21) Appl. No.: 16/273,848

(22) Filed: Feb. 12, 2019

(65) Prior Publication Data

US 2019/0247008 A1 Aug. 15, 2019

Related U.S. Application Data

(60) Provisional application No. 62/630,088, filed on Feb. 13, 2018.

(51) Int. Cl.
*A61F 7/02* (2006.01)
*A45F 5/02* (2006.01)
*A61B 7/02* (2006.01)

(52) U.S. Cl.
CPC .............. *A61B 7/02* (2013.01); *A45F 5/021* (2013.01); *A44D 2203/00* (2013.01)

(58) Field of Classification Search
CPC ... A44D 2203/00; A61B 7/02; Y10T 24/1394; Y10T 24/32
See application file for complete search history.

(56) References Cited

U.S. PATENT DOCUMENTS

| | | | |
|---|---|---|---|
| 3,797,717 A * | 3/1974 | Collins | A45C 11/00 224/230 |
| 5,025,966 A | 6/1991 | Potter | |
| 5,692,657 A * | 12/1997 | Kilo | A45F 5/02 224/269 |
| 6,065,563 A * | 5/2000 | Stowers | A45F 5/02 224/268 |
| 6,340,350 B1 * | 1/2002 | Simms | A61B 5/0002 D3/203.1 |
| 6,578,745 B1 | 6/2003 | Taylor et al. | |
| 8,037,965 B1 * | 10/2011 | Swink | A61B 7/02 181/135 |
| 8,499,986 B2 | 8/2013 | Knight et al. | |
| 9,009,922 B2 | 4/2015 | Perreault | |
| 9,249,814 B2 | 2/2016 | Tsai | |
| 10,512,292 B2 * | 12/2019 | Curtis | A41F 1/002 |
| 10,874,815 B2 * | 12/2020 | Haibach | A61M 11/00 |
| 11,324,289 B2 * | 5/2022 | Schapson | A44B 18/0073 |
| 2009/0026237 A1 | 1/2009 | Weaver | |
| 2010/0094151 A1 | 4/2010 | Baker et al. | |
| 2014/0317890 A1 | 10/2014 | Koons et al. | |

OTHER PUBLICATIONS

SNAP Female L Screw Fastener, Fidlock The reference is a webpage, and no date of publication is immediately apparent in the document, Applicants note that the webpage was printed on Aug. 28, 2019 and has a copyright date of 2019, however, the webpage may have been available, in some form, prior to this date. https:///www.fidlock.com/en/fasteners/snap/female-l-screw.html>, (2019).

* cited by examiner

*Primary Examiner* — Robert Sandy
(74) *Attorney, Agent, or Firm* — Knobbe Martens Olson & Bear, LLP

(57) ABSTRACT

This disclosure relates to stethoscope carrying devices and associated components such as clip and/or holder assemblies, systems, methods of manufacture and use.

20 Claims, 13 Drawing Sheets

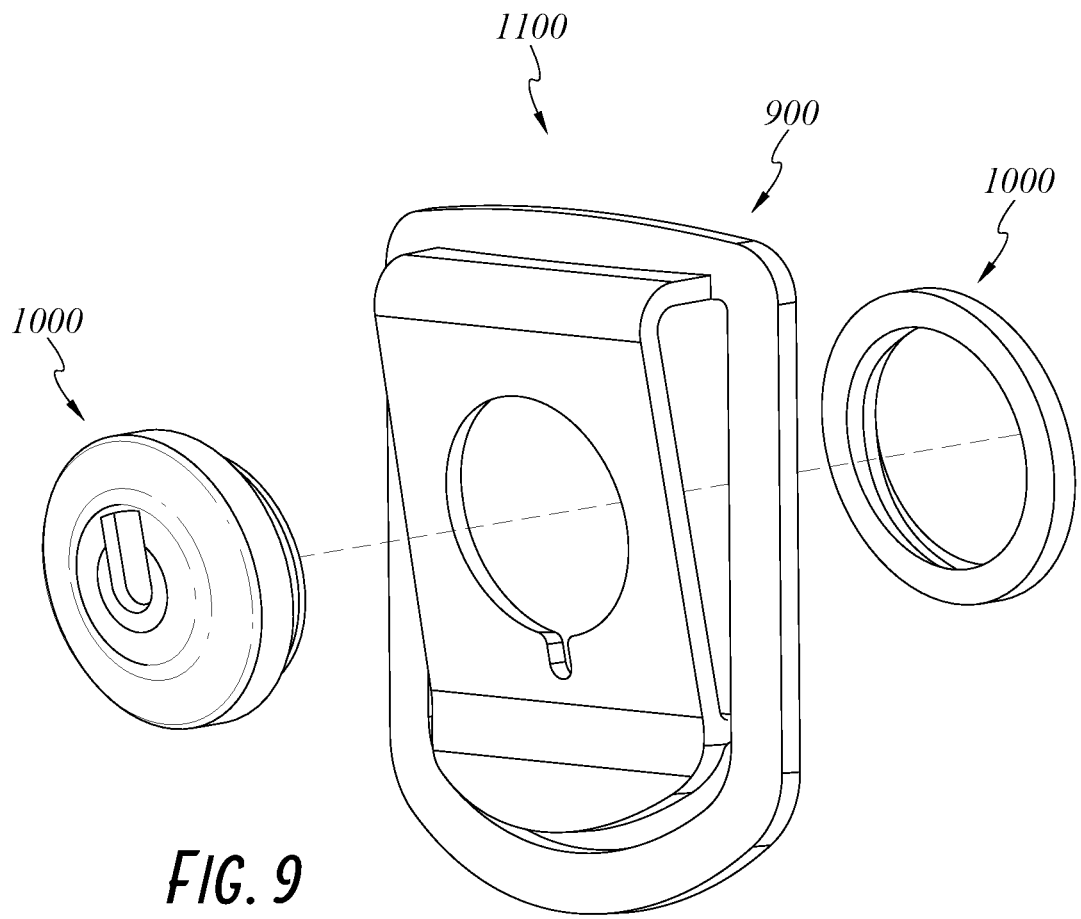
FIG. 9
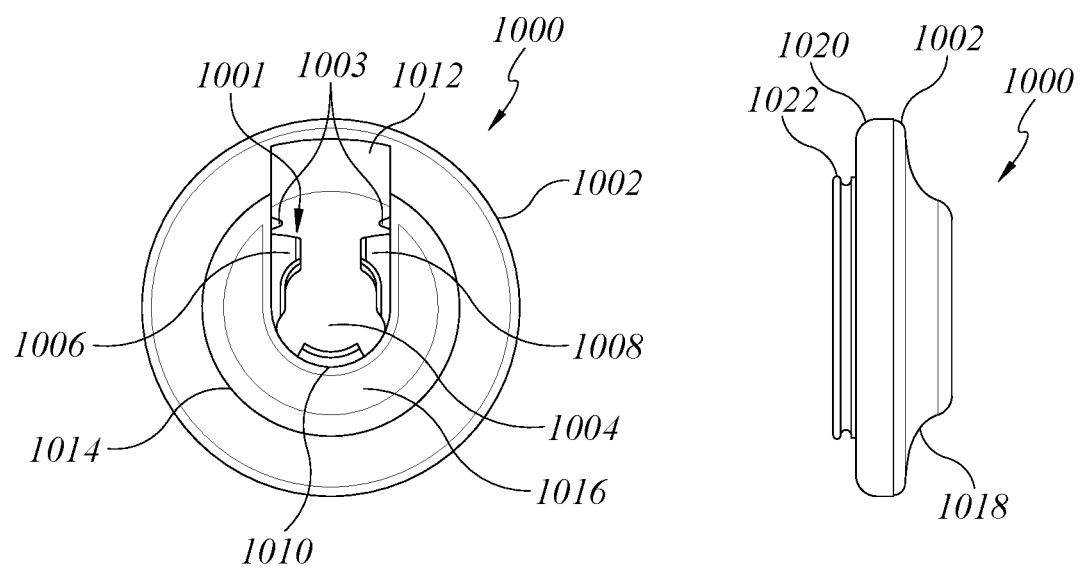
FIG. 10A
FIG. 10B

MAGNETIC CLIP STETHOSCOPE HOLDER

INCORPORATION BY REFERENCE TO ANY PRIORITY APPLICATIONS

This application claims the benefit under 35 U.S.C. § 119(e) as a nonprovisional application of U.S. Prov. App. No. 62/630,088 filed on Feb. 13, 2018, which is hereby incorporated by reference in its entirety. Any and all applications for which a foreign or domestic priority claim is identified in the Application Data Sheet as filed with the present application are hereby incorporated by reference under 37 CFR 1.57.

FIELD

This disclosure relates to stethoscope carrying devices and associated components such as clip and/or holder assemblies, systems, methods of manufacture and use.

BACKGROUND

A stethoscope is an important medical device that health care professionals use when interacting with patients. Health care professionals commonly carry a stethoscope around their necks or in a pocket. Wearing a stethoscope around one's neck can be problematic because it can cause neck strain, hang in inconvenient positions that can interfere with patient treatment, and/or inadvertently fall. Carrying a stethoscope in one's pocket can be problematic because it can be difficult to access quickly and/or inadvertently cause other objects to fall from one's pocket upon removal. It is desirable to have stethoscope carrying solutions which address these problems.

SUMMARY

Methods and apparatuses or devices disclosed herein each have several aspects, no single one of which is solely responsible for its desirable attributes. Without limiting the scope of this disclosure, for example, as expressed by the claims which follow, its more prominent features will now be discussed briefly.

The systems, methods, apparatuses, and devices of this disclosure can include a system for carrying a stethoscope. The system can have a chestpiece-securing assembly. The chestpiece-securing assembly can have a groove piece that can releasably couple to a tube of the stethoscope. The chestpiece-securing assembly can have a back piece that can releasably couple to the groove piece such that a fork region of the stethoscope is disposed between the groove piece and the back piece. The groove piece can position a headpiece of the stethoscope between binaural arms of the stethoscope, arranging the stethoscope in a folded position, when the groove piece is coupled to the tube of the stethoscope and the back piece. The system can have a magnetic clip assembly. The magnetic clip assembly can have a snap-fit device and a clip. The snap-fit device can have a magnetic receiving region and a locking mechanism. The locking mechanism can be disposed around a perimeter of the receiving region and have spring-loaded fasteners. The clip can be coupled to the snap-fit device and releasably couple to an item of clothing of a user. The system can have a male clip. The male clip can releasably couple to the tube of the stethoscope and mate with the magnetic receiving region of the snap-fit device and engage with the spring-loaded fasteners of the locking mechanism.

In some embodiments, the snap-fit device can have a recess. In some embodiments, the magnetic receiving region is a circle and disposed on a surface within a perimeter defined by the recess. In some embodiments, an internal perimeter of the recess is defined by a circle and a channel.

In some embodiments, the spring-loaded fasteners are favorably positioned such that the spring-loaded fasteners extend over the receiving region. In some embodiments, the spring-loaded fasteners can deflect to accommodate insertion of the male clip into the receiving region, and the spring-loaded fasteners can lock the male clip to the receiving region after insertion such that the male clip only decouples from the receiving region via sliding in a given direction.

In some embodiments, the male clip only couples to the receiving region by approaching the receiving region from a direction perpendicular to a surface of the receiving region or from a direction defined by a channel that is connected to the receiving region. In some embodiments, the male clip only decouples from the receiving region by sliding in a single direction determined by a channel connected to the receiving region.

In some embodiments, the male clip can be coupled to the tube of the stethoscope such that the male clip is positioned 2.5-5.5 inches away from a headpiece of the stethoscope. In some embodiments, the male clip can be coupled to the tube of the stethoscope such that the male clip is positioned 0.5-3.5 inches away from the chest-piece securing device when the stethoscope is in the folded position.

In some embodiments, the groove piece can have a groove defining a receiving region that couples to the tube of the stethoscope with a press fit. In some embodiments, the groove piece can have a plurality of support arms with a hook disposed on an end of each of the plurality of support arms, and the back piece can have a plurality of apertures configured to releasably couple to the hook disposed on each of the plurality of support arms.

In some embodiments, the hook of each of the plurality of support arms of the groove piece are releasably coupled to a surface proximate each of the plurality of apertures of the back piece with a snap fit. In some embodiments, the clip of the magnetic clip assembly can be clipped onto an item of clothing of the user with a snap fit.

In some embodiments, the male clip can have two arms that are configured to deflect around the tube of the stethoscope to form a press fit. In some embodiments, the male clip has a ferrous metal.

The systems, methods, apparatuses, and devices of this disclosure can include a system for carrying a stethoscope. The system can have a chestpiece-securing device. The chestpiece-securing device can couple to a fork region of the stethoscope and releasably couple to a tube of the stethoscope such that a headpiece of the stethoscope is positioned between binaural arms of the stethoscope. The system can have a magnetic clip. The magnetic clip can have a magnetic receiving region, a locking mechanism, and a clip. The locking mechanism can be disposed proximate to the magnetic receiving region and have spring-loaded fasteners. The clip can couple the magnetic clip to an item of clothing. The system can have a male clip. The male clip can releasably couple to the tube of the stethoscope and can make contact with the magnetic receiving region and interface with the spring-loaded fasteners of the locking mechanism.

In some embodiments, the male clip can couple to the tube of the stethoscope at a position that places the male clip 0.5-3.5 inches away from the chest-piece securing device when the chest-piece-securing device is coupled to the fork region and tube of the stethoscope such that the headpiece of the stethoscope is positioned between binaural arms of the stethoscope.

The systems, methods, apparatuses, and devices of this disclosure can include a system for carrying a stethoscope. The system can have a chestpiece-securing device. The chestpiece-securing device can couple to a fork region of the stethoscope and releasably couple to a tube of the stethoscope such that the stethoscope is in a folded position. The system can have a magnetic clip. The magnetic clip can have a magnetic receiving region, mechanical fasteners, and a clasp. The mechanical fasteners can be positioned proximate a perimeter of the magnetic receiving region. The clasp can couple the magnetic clip to an item of clothing. The system can have a male clip. The male clip can releasably couple to the tube of the stethoscope and can magnetically couple to the receiving region and engage with the mechanical fasteners of the magnetic clip.

In some embodiments, the male clip can be coupled to the tube of the stethoscope at a position that places the male clip 0.5-3.5 inches away from the chest-piece securing device when the stethoscope is in the folded position.

BRIEF DESCRIPTION OF THE DRAWINGS

Various embodiments are depicted in the accompanying drawings for illustrative purposes and may not be drawn to scale, and should in no way be interpreted as limiting the scope of the embodiments. In addition, various features of different disclosed embodiments can be combined to form additional embodiments, which are part of this disclosure. In the drawings, similar elements may have reference numerals with the same last two digits.

FIG. 9 is an illustrative example of an exploded view of a magnetic clip assembly.

FIG. 10A is an illustrative example of a front view of a snap-fit device.

FIG. 10B is an illustrative example of a side view of a snap-fit device.

DETAILED DESCRIPTION

Figure 1:
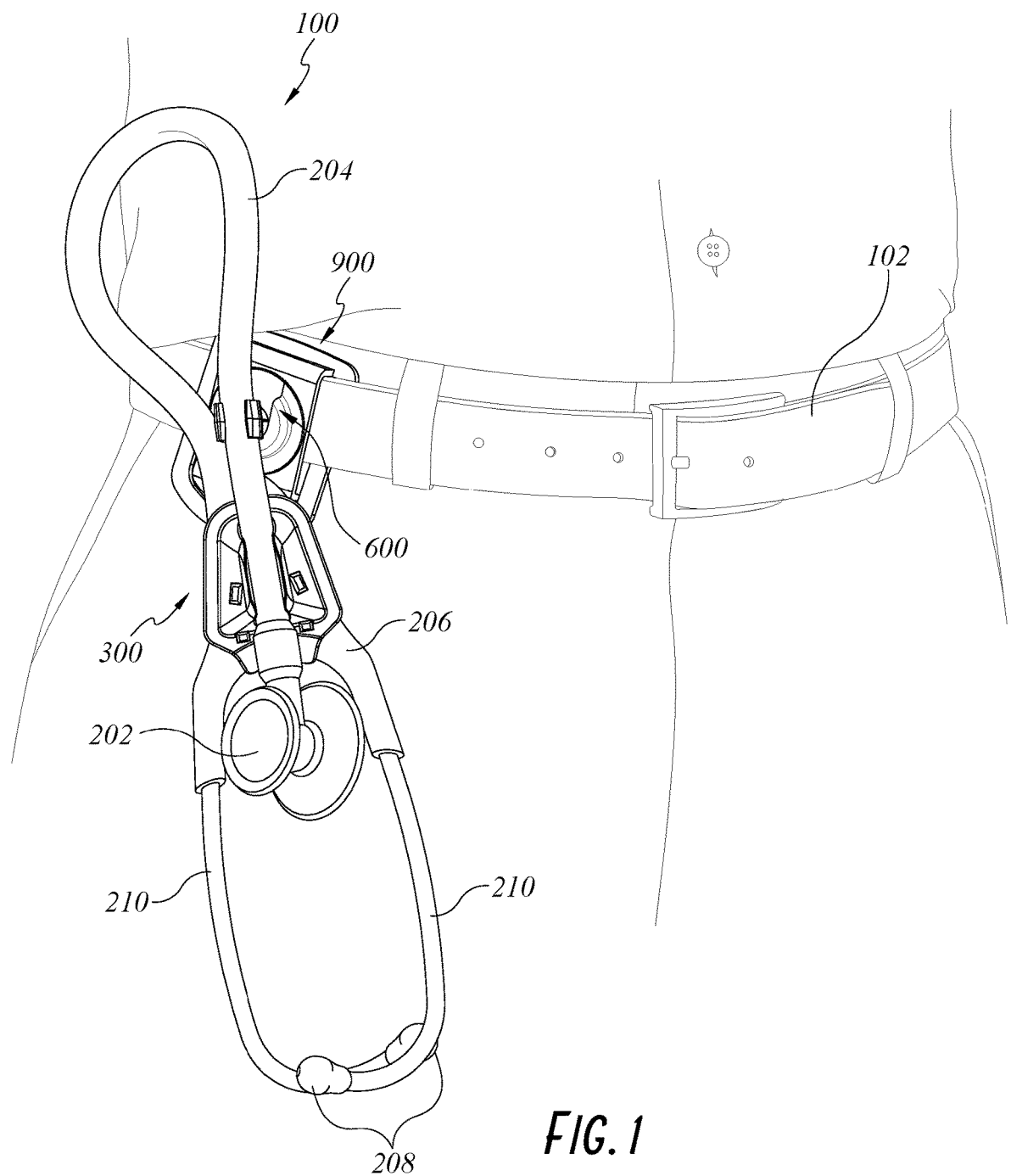
FIG. 1 is an illustrative example of a stethoscope carrying system in use.

In the following detailed description, reference is made to the accompanying drawings, which form a part thereof. In the drawings, similar symbols typically identify similar components, unless context dictates otherwise. Thus, in some embodiments, part numbers may be used for similar components in multiple figures, or part numbers may vary depending from figure to figure. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and made part of this disclosure.

Example Stethoscope Carrying System

FIG. 1 depicts an example stethoscope carrying system 100 clipped onto the belt of a user 102. In some embodiments, user 102 is a health care professional. The stethoscope carrying system 100 can be configured to allow a user to maintain a stethoscope in a convenient position/location for easy retrieval and storage. The stethoscope carrying system 100 can be configured to allow a user to attach a stethoscope to a clip, such as a belt clip positioned on the user, with one hand and/or without looking. The stethoscope carrying system 100 can be configured to prevent the stethoscope from inadvertently dislodging during routine activity. The stethoscope carrying system 100 can be configured to only decouple from a clip, such as a belt clip positioned on the user, with a deliberate decoupling movement by the user, such as pulling in an upward direction. The stethoscope carrying system 100 can be configured to position the stethoscope in a folded position that will prevent the stethoscope from swinging freely while an individual is ambulating. The stethoscope carrying system 100 can be configured to easily clip onto the belt, waistband, and/or other item of clothing of a user. The stethoscope carrying system 100 and a stethoscope can be configured to be removed together, while coupled together, from being attached to an item of clothing of a user.

Figure 2:
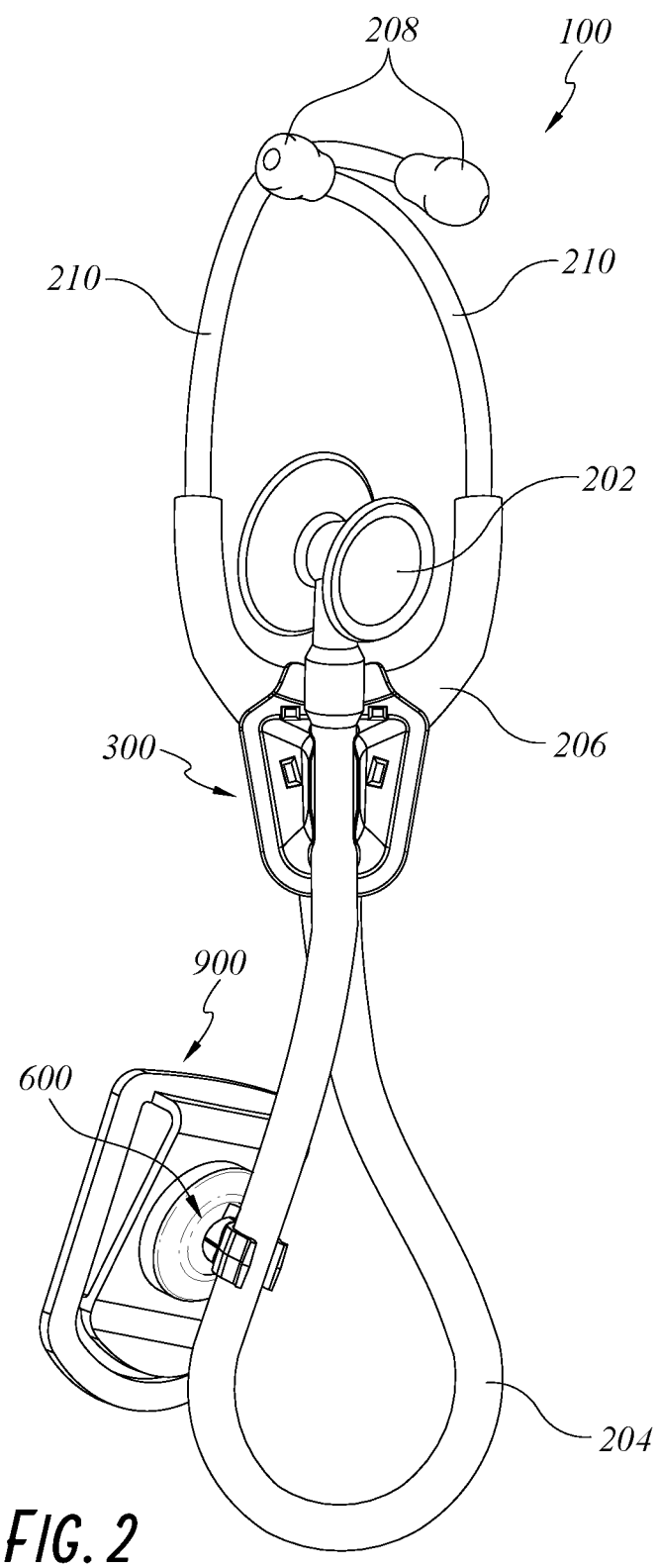
FIG. 2 is an illustrative example of a stethoscope carrying system.

FIG. 2 depicts an example stethoscope carrying system 100 that is configured to facilitate carrying stethoscope 200.

Stethoscope 200 can have two ear pieces 210 that are connected to a fork 206 via binaural arms 210. The fork 206 can be connected to a headpiece 202 via a tube 204. Tube 204 can be flexible.

A chestpiece-securing assembly 300 can be positioned at the fork 206. In some embodiments, the chestpiece-securing assembly 300 is arranged such that the fork 206, or a portion of the fork 206, is positioned between components of the chestpiece-securing assembly 300. The chestpiece-securing assembly 300 can releasably couple to the tube 204 of the stethoscope 200, such that the stethoscope 200 is arranged in a folded position. In some embodiments, this configuration can position the headpiece 202 between the binaural arms 210 of the stethoscope 200. In some embodiments, this configuration can prevent the stethoscope 200 from swinging while a user is ambulating and/or otherwise moving. In some embodiments, this configuration can form a loop with tube 204.

A male clip assembly 600 can be releasably clipped onto any position on the tube 204. In some embodiments, the male clip assembly 600 is releasably clipped onto the tube 204 at a position that is 2-7 inches from the headpiece 202. In some embodiments, the male clip assembly 600 is releasably coupled onto the tube 204 at a position that is 3-5 inches from the headpiece 202. In some embodiments, the male clip assembly 600 is releasably coupled onto the tube 204 at a position that is configured to be ½-3 inches from the chestpiece-securing assembly 300 when the stethoscope carrying system 100 is placed into a folded position. In some embodiments, the male clip assembly is releasably coupled onto the tube 204 at a position that is configured to be 1-2 thumbs away from the chestpiece-securing assembly 300 when the stethoscope carrying system 100 is placed into a folded position. Positioning the male clip assembly 600 in a position on tube 204 that is generally close in proximity to the headpiece 202 and/or chest-piece-securing assembly 300 (including some and/or all the ranges listed above) can prevent the stethoscope from swinging while a user is ambulating and/or moving. In some embodiments, this configuration can reduce (or eliminate) the likelihood that the stethoscope 200 will dangle in positions that will catch on other objects when being carried. The male clip assembly 600 can releasably couple to a magnetic clip assembly 900. The magnetic clip assembly 900 can be configured to only decouple from male clip assembly 600 when male clip assembly 600 is grasped and moved in a given direction, such as upward. This can reduce unintentional decoupling, while still facilitating quick decoupling of the male clip assembly 600 from the magnetic clip assembly 900. The magnetic clip assembly 900 can releasably couple to an item of clothing of a user. In some embodiments, the magnetic clip assembly 900 clips onto the belt of a user and/or a waistband.

A user can freely move with the stethoscope 200 secured in a folded position and clipped onto an item of clothing, such as a belt, as is shown in FIG. 1. For convenience, this is referred to as the "carry position." In some embodiments, the carry position prevents the stethoscope 200 from swinging while a user is ambulating and/or otherwise moving. In some embodiments, swinging is minimized when the male clip assembly 600 is releasably coupled onto the tube 204 at a position that is configured to be ½-3 inches from the headpiece 202 when the stethoscope carrying system 100 is placed into the folded position. The user can quickly remove the stethoscope 200 from the carry position by grasping the male clip assembly 600 and moving the male clip assembly 600 in a given direction, dictated by the configuration of the magnetic clip assembly 900. The user can unfold the stethoscope 200 by decoupling the tube 204 from the chestpiece-securing assembly 300. When a user is using the stethoscope 200 on a patient, the chestpiece-securing assembly 300 can remain coupled to the fork 206 and the male clip assembly 600 can remain coupled to the tube 204. The user can quickly arrange the stethoscope 200 in the carry position by coupling the chestpiece securing assembly 300 to the tube 204 and coupling the male clip assembly 600 to the magnetic clip assembly 900. This configuration can allow a user to store the stethoscope 200 in the carry position or remove the stethoscope 200 from the carry position while maintaining eye contact with a patient. In some embodiments, the stethoscope carrying system 100 can rotate when a user sits when the stethoscope 200 is in the carry position. The headpiece 202 and binaural arms 210 of the stethoscope 200 can be make contact with and be pushed by the thigh, which can include the inner thigh, of a user as the user sits. This can cause the stethoscope 200 and chestpiece-securing assembly 300 to rotate at the coupling point between the male clip assembly 600 and the magnetic clip assembly 900. The rotation can be such that the headpiece securing assembly 900 and binaural arms 210 of the stethoscope 200 are rotated counterclockwise.

In some embodiments, a user does not place the stethoscope 200 into a folded position when utilizing the stethoscope carrying system 100. Rather, the user couples the male clip assembly 600 to the magnetic clip assembly 900 without folding the stethoscope 200 and/or coupling the tube 204 to the chestpiece-securing assembly 300.

Example Chestpiece-Securing Assembly

Figure 3A:
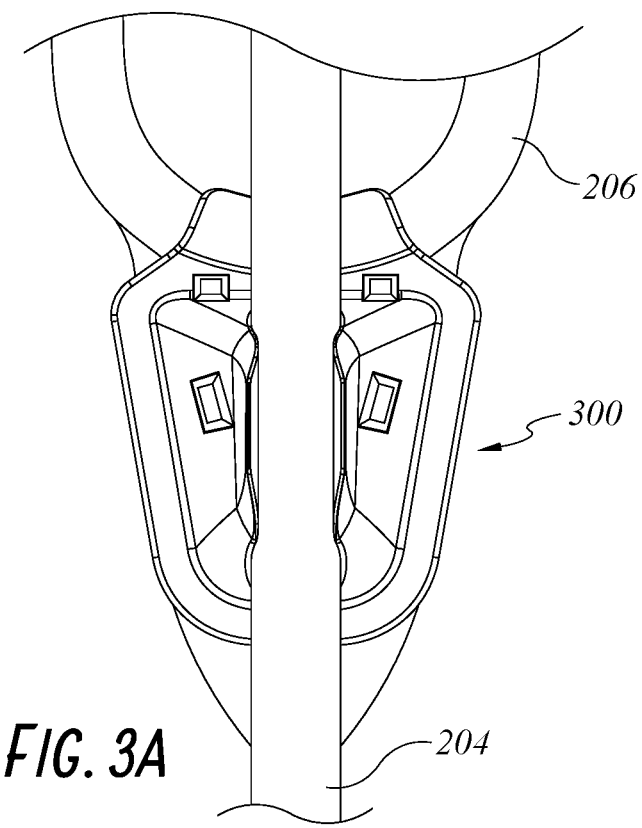
FIG. 3A is an illustrative example of a chestpiece-securing assembly coupled to a stethoscope.
Figure 3B:
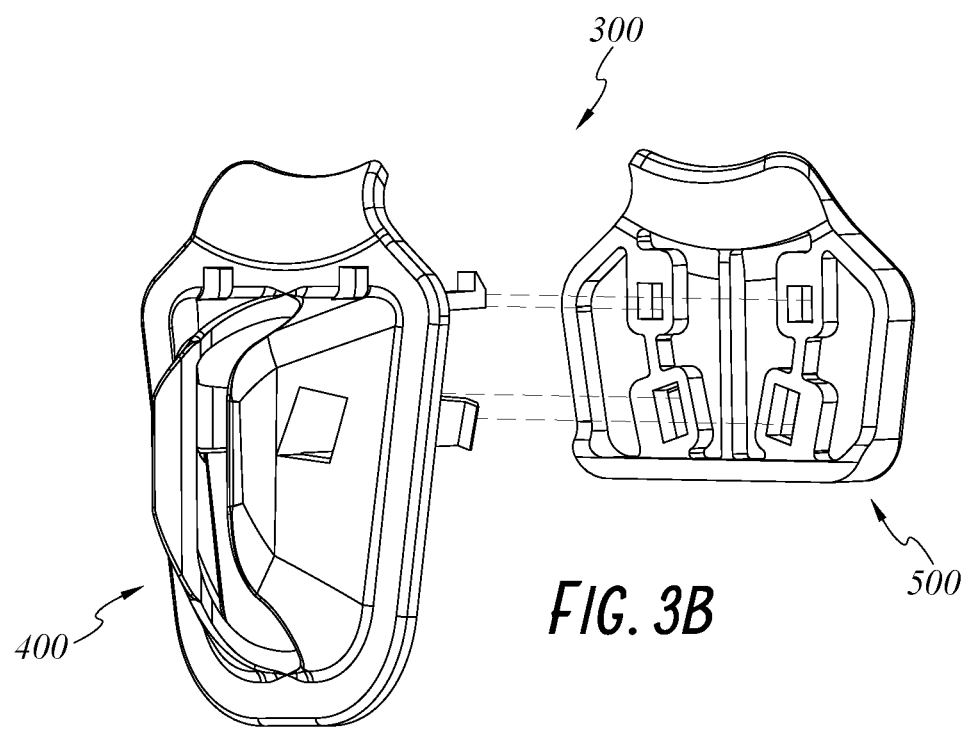
FIG. 3B is an illustrative example of an exploded view of a chestpiece assembly.
Figure 4A:
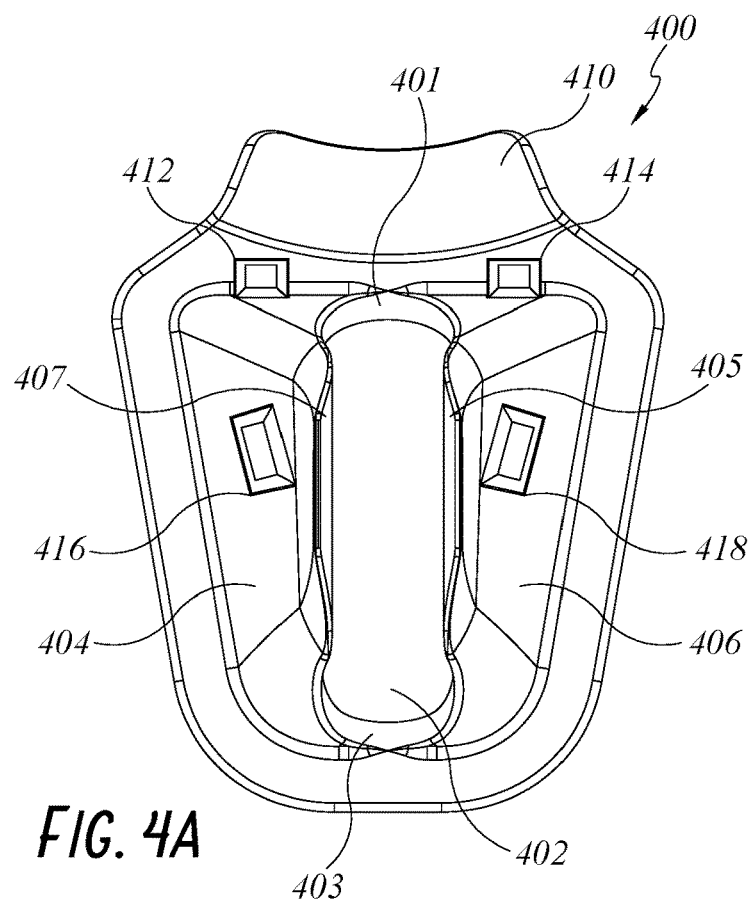
FIG. 4A is an illustrative example of a front view of a groove piece.
Figure 4B:
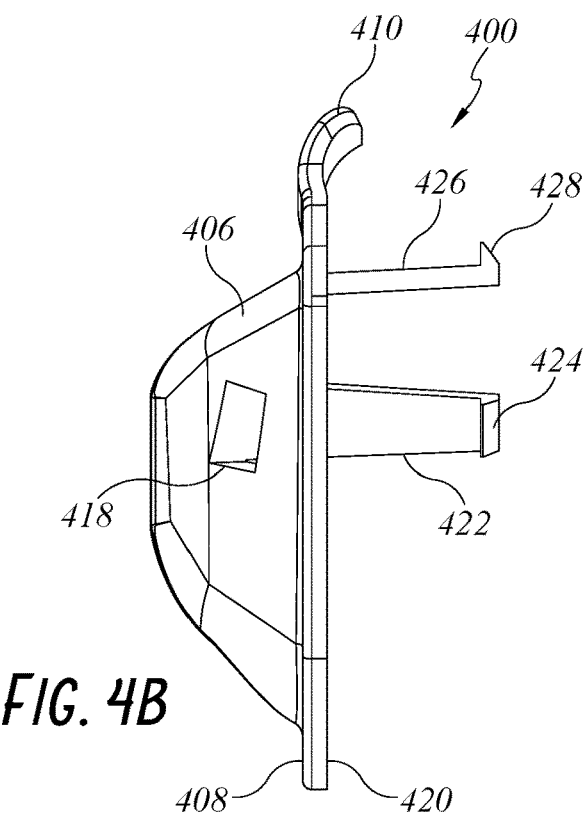
FIG. 4B is an illustrative example of a side view of a groove piece.
Figure 4C:
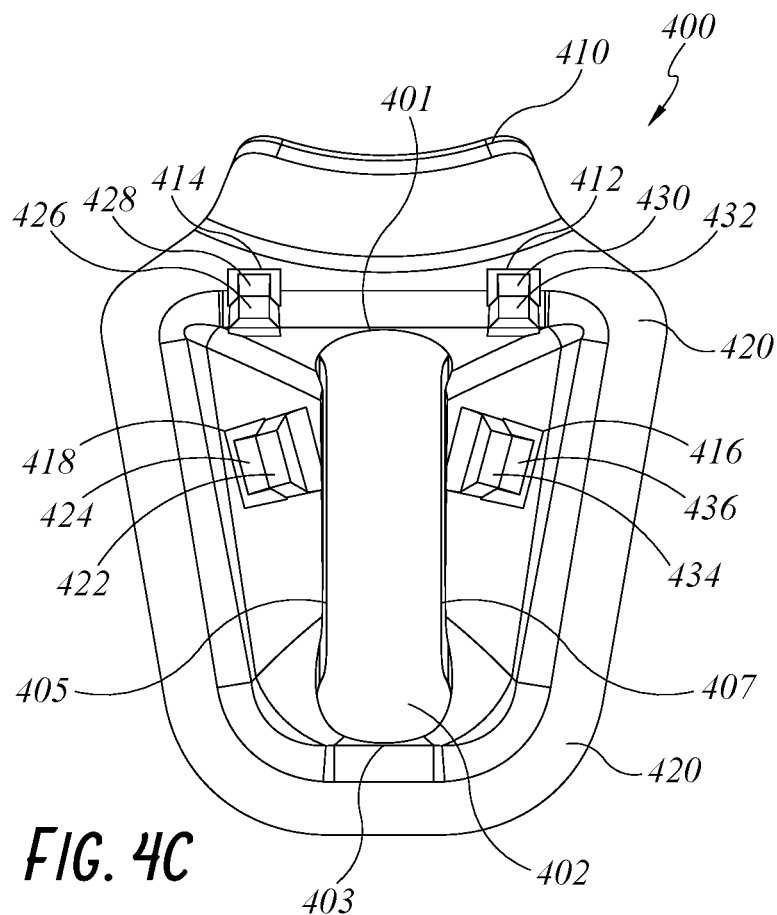
FIG. 4C is an illustrative example of a back view of a groove piece.
Figure 4D:
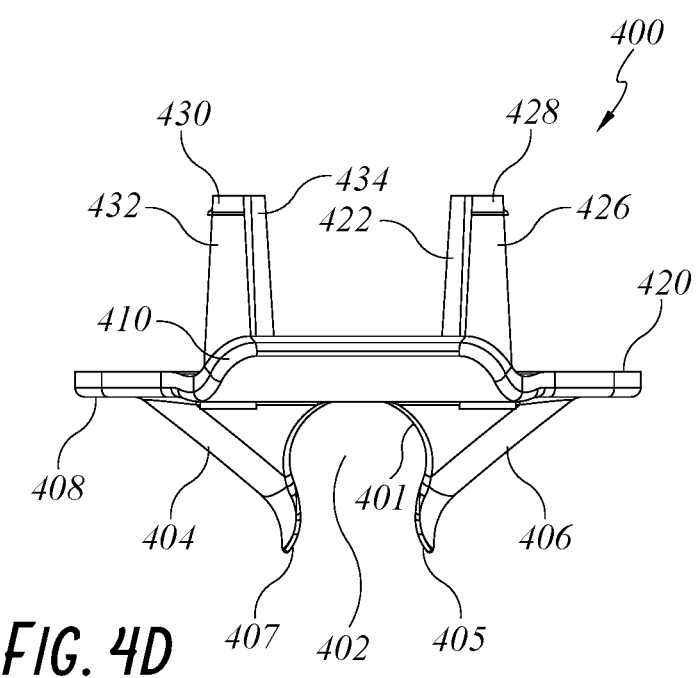
FIG. 4D is an illustrative example of a top view of a groove piece.
Figure 4E:
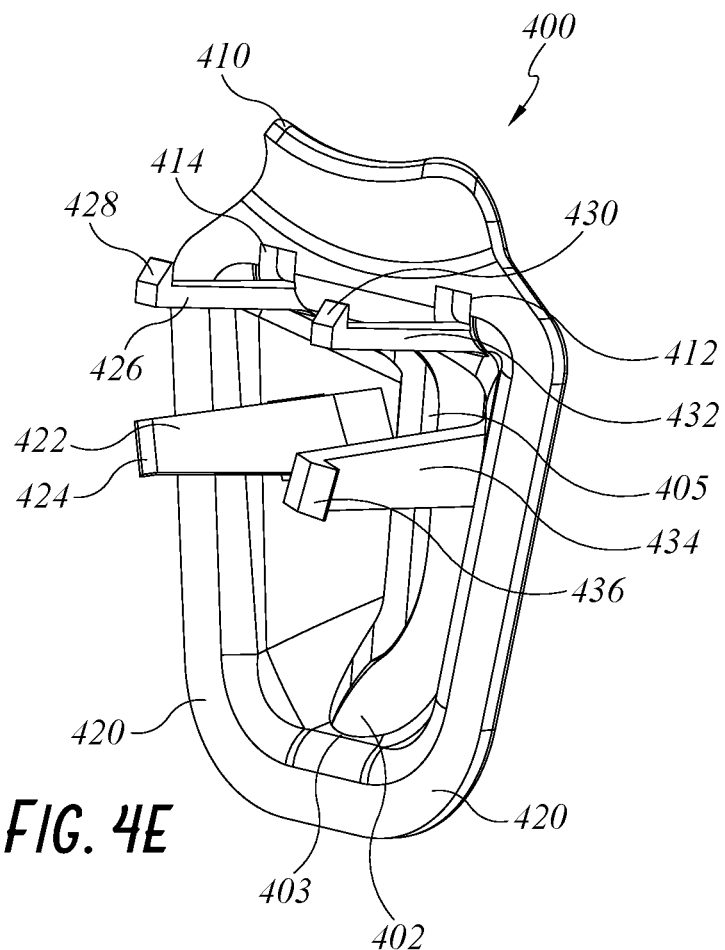
FIG. 4E is an illustrative example of a back perspective view of a groove piece.
Figure 5A:
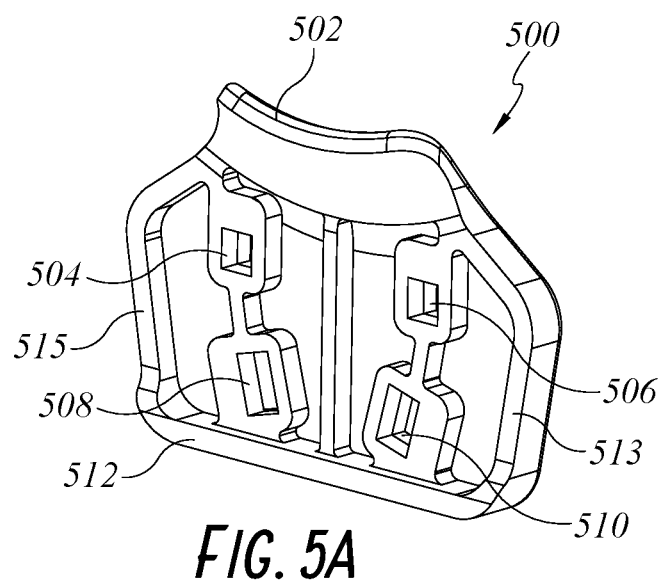
FIG. 5A is an illustrative example of a perspective view of a back piece.
Figure 5B:
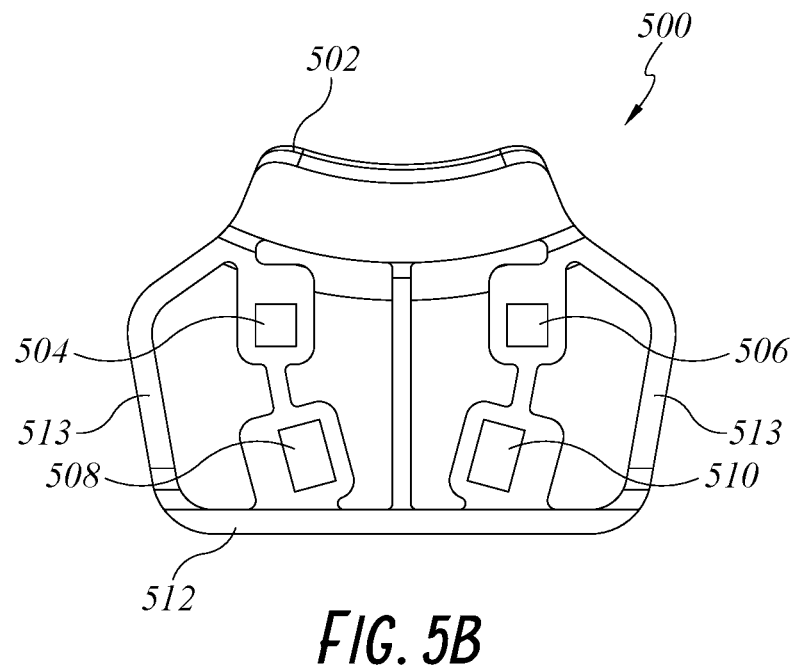
FIG. 5B is an illustrative example of a front view of a back piece.
Figure 5C:
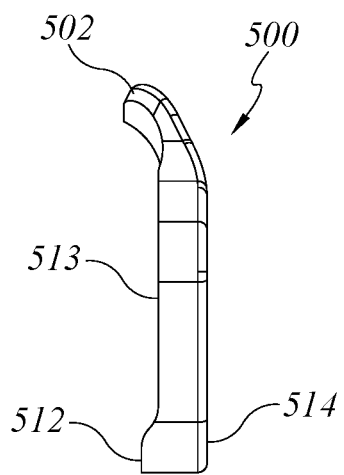
FIG. 5C is an illustrative example of a side view of a back piece.
Figure 5D:
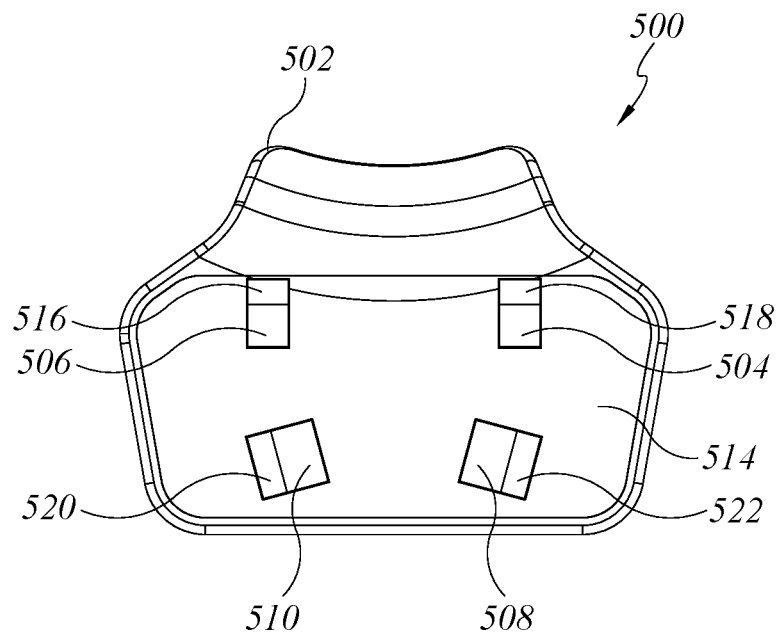
FIG. 5D is an illustrative example of a back view of a back piece.
Figure 5E:
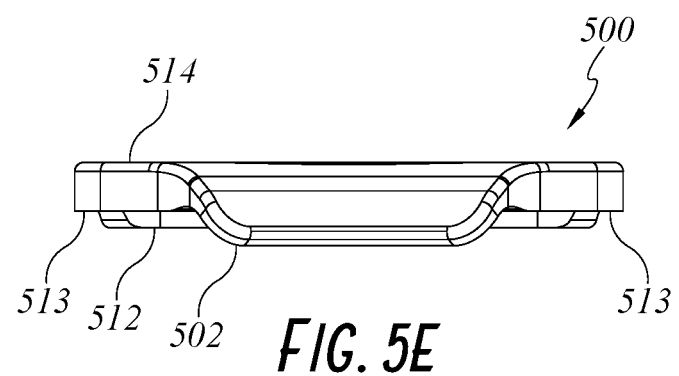
FIG. 5E is an illustrative example of a top view of a back piece.

FIGS. 3A and 3B depict an example chestpiece-securing assembly 300. The chestpiece-securing assembly 300 can couple, which can include releasably coupling, to the fork 206 of stethoscope 200. The chestpiece-securing assembly 300 can releasably couple to the tube 204, which can include a press fit.

The chestpiece-securing assembly 300 can have a groove piece 400 that can couple to back piece 500. The fork 206, or a portion of the fork 206, can be positioned between the groove piece 400 and the back piece 500, securing the chestpiece-securing assembly 300 onto stethoscope 200.

In some embodiments, the chestpiece-securing assembly 300 is a singular component that couples to the fork 206 and/or portion of the tube 204 proximate the fork 206. In some embodiments, chestpiece-securing assembly 300 is groove piece 400 but includes additional claps that allow the groove piece 400 to clasp onto at least a portion of the fork 206 and/or a portion of tube 204 without back piece 500.

FIGS. 4A-4E depict an example groove piece 400. The groove piece 400 can have extrusions 404, 406. Extrusions 404, 406 can extend to be offset from surface 408. Extrusions 404,406 can define a receiving region 402 that is configured to releasably couple to the tube 204, which can include coupling with a press fit. Receiving region 402 can include curves 401, 403 positioned on opposing sides of the receiving region 402. Curves 401, 403 can be positioned coaxially. Curves 401, 403 can be sized and dimensioned to receive the tube 204. In some embodiments, the curves 401, 403 can have a radius of 4-7 mm. In some embodiments, an insert can be placed in the receiving region 402 to allow the receiving region 402 to accommodate tubes 204 of varying sizes, allowing the receiving region to at least receive the two most common tube 204 sizes for stethoscopes 200.

Receiving region 402 can have retaining edges 405, 407. Retaining edges 405, 407 can be arranged on a position on extrusions 404, 406 that is farthest from surface 408. Retaining edges 405, 407 can be positioned parallel to the coaxial axis defined by curves 401, 403. Retaining edge 405 can be positioned opposite retaining edge 407. Retaining edges 405 and 407 can be positioned such that tube 204 can be positioned in the receiving region 402 with a press fit. In some embodiments, retaining edge 405 can be offset from retaining edge 407 by 7-13 mm. In some embodiments, retaining edges 405, 407 can each have a curve that is configured to facilitate tube 404 being press fit through the gap defined between retaining edges 405, 407. In some embodiments, the curves of retaining edges 405, 407 are connected to curves 401, 403. In some embodiments, extrusions 404, 406 have narrower cross-sections proximate retaining edges 404, 407 than proximate surface 408.

A curve 410 can be disposed on a top end of groove piece 400. Curve 410 can be configured to interface with a top segment of fork 406 that is positioned between binaural arms 210. In some embodiments, curve 410 can have a radius similar to the top segment of fork 406 that is positioned between binaural arms 210. The curve 410 can curve in a direction opposite the receiving region 402.

The groove piece 400 can have a plurality of apertures, such as top apertures 412, 414 and bottom apertures 416, 418. Top apertures 412, 414 can be positioned on opposing sides of the receiving region 402. Top apertures 412, 414 can be any shape. In some embodiments, top apertures 412, 414 can be rectangles. Top apertures 412, 414 can be positioned such that they are equidistantly spaced away from the receiving region 402. Top apertures 412, 414 can be positioned on surface 408 and/or extrusions 404, 406. Top apertures 412, 414 can be positioned proximate curve 410.

Bottom apertures 416, 418 can be positioned on opposing sides of the receiving region 402. Bottom apertures 416, 418 can be any shape. In some embodiments, bottom apertures 416, 418 can be rectangles. Bottom apertures 416, 418 can be positioned such that they are equidistantly spaced away from the receiving region 402. Bottom apertures 416, 418 can be positioned on surface 408 and/or extrusions 404, 406.

Groove piece 400 can have a plurality of support arms, such as top support arms 426, 430 and bottom support arms 422, 434. The plurality of support arms can be positioned on a side of groove piece opposite the retaining region 402, which can include the opposing side of extrusions 404, 406. The plurality of support arms can extend in a direction that is perpendicular to a plane defined by the contact face 420. The plurality of support arms can extend in a direction opposite the receiving region 402. The plurality of support arms can be positioned such that the longitudinal axis of each of the plurality of support arms is parallel. In some embodiments, the plurality of arms have a uniform size, which can include cross-section. In some embodiments, each of the plurality of arms can have a cross-section that becomes smaller in the direction extending opposite the receiving region 402. In some embodiments, the cross-section of top support arms 426, 430 are smaller than the cross-section of bottom support arms 422, 434.

Top support arm 426 can be positioned proximate top aperture 414. Top support arm 430 can be positioned proximate top aperture 412. Bottom support arm 422 can be positioned proximate bottom aperture 418. Bottom support arm 434 can be positioned proximate bottom aperture 416. Top support arms 426, 430 and bottom support arms 422, 434 can have cross-sections that are any shape. In some embodiments, Top support arms 426, 430 and bottom support arms 422, 434 can have cross-sections that are rectangles. Top support arms 426, 430 and bottom support arms 422, 434 can extend an equidistant distance away from a plane defined by contact surface 420.

Top support arm 426 can have a top hook 428 disposed on and/or proximate an end. Top support arm 432 can have a top hook 430 disposed on and/or proximate an end. Bottom support arm 422 can have a bottom hook 424 disposed on and/or proximate an end. Bottom support 434 can have a bottom hook 436 disposed on and/or proximate an end. Top hooks 428, 430 and bottom hooks 424, 436 can be configured to snap fit to the back piece 500 such that the groove piece 400 is coupled to the back piece 500. In some embodiments, top hooks 428, 430 are oriented in the same direction. In some embodiments, bottom hooks 424, 436 are each oriented at an angle from the coaxial axis defined by curves 401, 403.

FIGS. 5A-5E depict an example back piece 500. Back piece 500 can have a curve 502 positioned on an end. Curve 502 can have the same characteristics as curve 410. Curve 502 can be configured to interface with a top segment of fork 206 that is positioned between binaural arms 210.

Back piece 500 can have a contact surface 512 disposed on a side that that will make contact with the fork 206. Contact surface 512 can be raised from surfaces 513 such that the curve 502 and contact surface 512 will make contact with fork 206 when chestpiece-securing assembly 300 is coupled to the fork 206.

Back piece 500 can have a plurality of apertures, which can include top receiving apertures 504, 506 and bottom receiving apertures 508, 510. The plurality of apertures can be configured to receive the plurality of arms of the groove piece 400, such that the groove piece 400 is coupled to the back piece 500.

The plurality of apertures can be proximate bevels which interface with the hooks of the plurality of arms to facilitate a snap fit connection between the groove piece 400 and the back piece 500. In some embodiments, the plurality of arms and/or hooks deflect to create a snap fit connection as the groove piece 400 is coupled to the back piece 500. In some embodiments, the plurality of arms and/or hooks deflect to uncouple a snap fit connection when the groove piece 400 is decoupled form the back piece 500.

The top receiving aperture 504 can include a proximately positioned bevel 518 that extends from the back surface 514 to the top receiving aperture 504. In some embodiments, top support arm 432 can extend through top receiving aperture 504, snapping hook 430 into a position that interfaces with bevel 518 to create a snap fit. The top receiving aperture 506 can include a proximately positioned bevel 516 that extends from the back surface 514 to the top receiving aperture 506. In some embodiments, top support arm 426 can extend through top receiving aperture 506, snapping hook 428 into a position that interfaces with bevel 516 to create a snap fit. The bottom receiving aperture 508 can include a proximately positioned bevel 522 that extends from the back surface 514 to the bottom receiving aperture 508. In some embodiments, bottom support arm 434 can extend through bottom receiving aperture 508, snapping hook 436 into a position that interfaces with bevel 522 to create a snap fit. The bottom receiving aperture 510 can include a proximately positioned bevel 520 that extends from the back surface 514 to the bottom receiving aperture 510. In some embodiments, bottom support arm 422 can extend through bottom receiving aperture 510, snapping hook 424 into a position that interfaces with bevel 520 to create a snap fit.

In some embodiments, a sticker, name label, and/or cover plate can be positioned on back face 514.

Example Male Clip Assembly

Figure 6A:
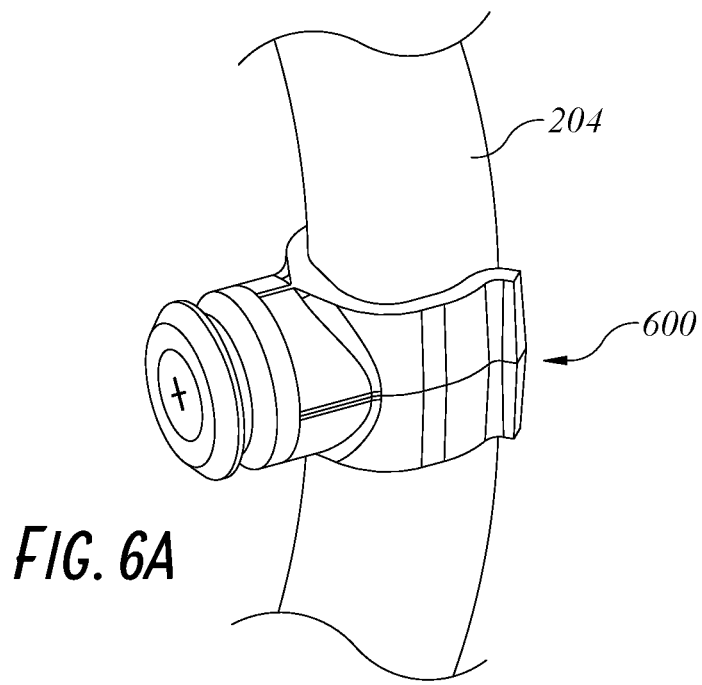
FIG. 6A is an illustrative example of a male clip assembly coupled to a stethoscope.
Figure 6B:
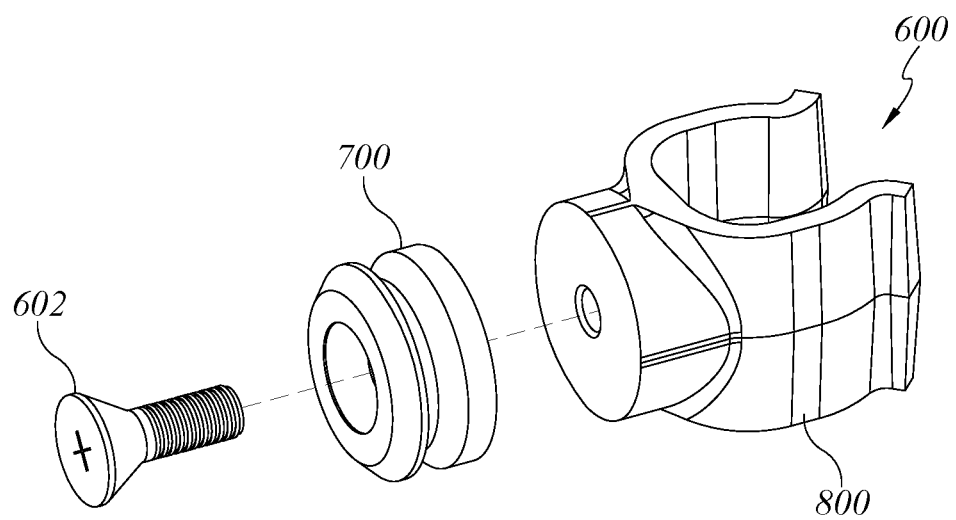
FIG. 6B is an illustrative example of a male clip assembly.

FIGS. 6A-6B depict an example male clip assembly 600. Male clip assembly 600 can couple to a tube 204 of stethoscope 200. In some embodiments, the male clip assembly 600 is releasably coupled to tube 204 of stethoscope 200 with a press fit. In some embodiments, male clip assembly 600 is releasably coupled to any location on the tube 204. In some embodiments, the male clip assembly 600 is releasably clipped onto the tube 204 at a position that is 2-7 inches from the headpiece 202. In some embodiments, the male clip assembly 600 is releasably coupled onto the tube 204 at a position that is 3-5 inches from the headpiece 202. In some embodiments, the male clip assembly 600 is releasably coupled onto the tube 204 at a position that is configured to be ½-3 inches from the chestpiece-securing assembly 300 when the stethoscope carrying system 100 is placed into a folded position. In some embodiments, the male clip assembly is releasably coupled onto the tube 204 at a position that is configured to be 1-2 thumbs away from the chestpiece-securing assembly 300 when the stethoscope carrying system 100 is placed into a folded position.

Male clip assembly 600 can have a screw 602, mating member 700, and tube clasp 800. Screw 602 can couple mating member 700 and tube clasp 800. In some embodiments, male clip assembly 600 is a singular component, not an assembly, that can couple to tube 204 and magnetic clip assembly 900.

Figure 7A:
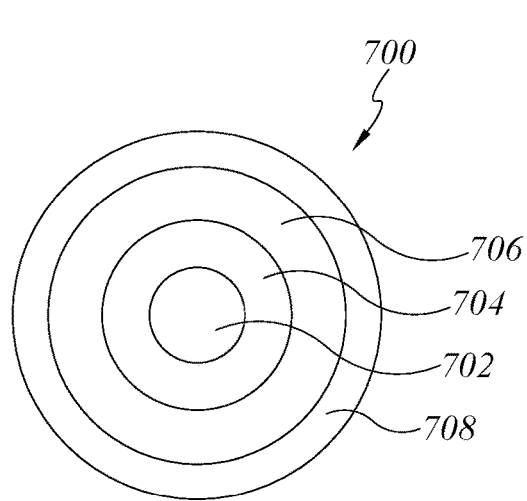
FIG. 7A is an illustrative example of a front view of a mating piece.
Figure 7B:
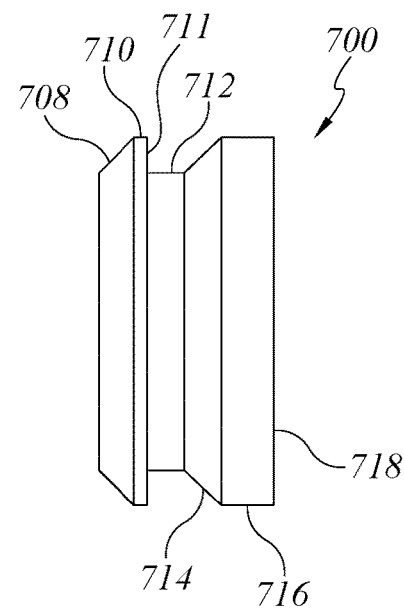
FIG. 7B is an illustrative example of a side view of a mating piece.

FIGS. 7A-7B depict an example mating member 700. Mating member 700 can have an aperture 702, which can have a circular cross-section. The diameter of aperture 702 can be sized to allow at least a portion of the threaded portion of screw 602 to be housed inside aperture 702. Aperture 702 can have any size. Aperture 702 can extend through the entirety of mating member 700. In some embodiments, aperture 702 has threads. In some embodiments, aperture 702 has an inside perimeter that is smooth such that threads of screw 602 can slide unobstructed.

A mating surface 706 can define a ring that is positioned coaxially with the aperture 702. In some embodiments, mating surface 706 is any shape. Mating surface 706 can be perpendicular to the axis of aperture 702. Mating surface 706 can be centered around aperture 702. A bevel 704 can be positioned between the aperture 702 and mating surface 706, such that the mating surface 706 is offset from the opening of aperture 702. Bevel 704 can be sized such that the top surface of the head of screw 602 is flush with mating surface 706 when screw 602 is inserted into aperture 702.

A bevel 708 can be positioned around an outer perimeter of the mating surface 706. In some embodiments, bevel 708 is sized and dimensioned to facilitate deflection of spring-loaded fastener 1001, also referred to as a mechanical snap feature and/or mechanical snap mechanism, described in reference to FIGS. 10A-10B, such that mating member 700 can couple with magnetic clip assembly 900. Bevel 708 can be disposed between the outer perimeter of mating surface 706 and surface 710. Surface 710 can define an outer cylindrical perimeter of mating member 700.

A retaining surface 711 can be positioned adjacent to surface 710. Retaining surface 711 can extend transversely inward from surface 710. In some embodiments, the retaining surface 711 extends from the surface 710 at a ninety degree angle. Retaining surface 711 can be configured to engage with spring-loaded fastener 1001 such that the mating member 700 is releasably coupled to magnetic clip assembly 900. Recess surface 712 can extend transversely from retaining surface 711. In some embodiments, the recess surface 712 extends from the retaining surface 711 at a ninety degree angle. Recess surface 712 can be configured to engage with spring-loaded fastener 1001 such that the mating member 700 is releasably coupled to magnetic clip assembly 900.

A bevel 714 can transition from the diameter defined by the recess surface 712 to the diameter defined by surface 716. The diameter defined by surface 716 can be the same as the diameter defined by surface 710.

A contact surface 718 can be on an end of mating member 700 that is opposite mating surface 706. Contact surface 718 can be perpendicular to the axis of aperture 702. Contact surface 718 can be any shape. The shape of contact surface 718 can be defined by the perimeter defined by surface 716. Contact surface 718 can be circular. Contact surface 718 can be disrupted by aperture 702. Contact surface 718 can be configured to be positioned flush with contact surface 806 of tube clasp 800, described in reference to FIGS. 8A and 8B. In some embodiments, contact surface 718 has the same size and shape as contact surface 806.

In some embodiments, mating member 700 can be made of a ferrous metal such that mating member can magnetically interface with the magnetic clip assembly 900. In some embodiments, the mating member 700 is made of steel.

Figure 8A:
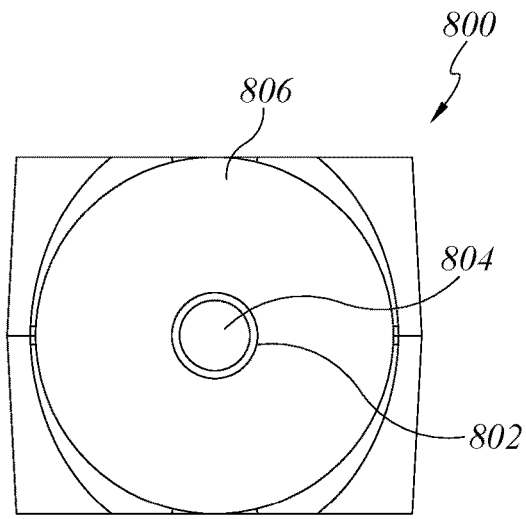
FIG. 8A is an illustrative example of a front view of a tube clasp.
Figure 8B:
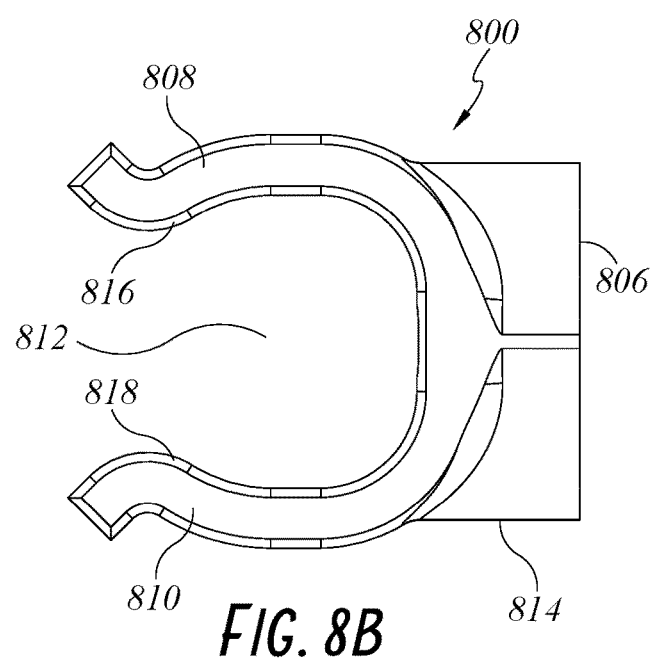
FIG. 8B is an illustrative example of a top view of a tube clasp.

FIGS. 8A-8B depict an example tube clasp 800. Tube clasp 800 can have an aperture 802. Aperture 802 can be threaded such that the screw 602 can be screwed into aperture 802 in order to couple the tube clasp 800 to the mating member 700. In some embodiments, aperture 802 can be configured to receive a threaded insert such that the screw 602 can be screwed into aperture 802. Aperture 802 can extend through the entirety of tube clasp 800. In some embodiments, aperture 802 extends partially through tube clasp 800. In some embodiments, aperture 802 can have the same diameter as aperture 702.

In some embodiments, a bevel 804 can be positioned between contact surface 806 and aperture 804 such that the contact surface 806 is offset from the opening of aperture 804. Contact surface 806 can be configured to interface with contact surface 718 of mating portion 700 such that contact surface 806 is flush with contact surface 718 when tube clasp 800 is coupled to mating member 700. In some embodiments, contact surface 806 can be sized and shaped similarly or equivalently to contact surface 718. Contact surface 806 can be any shape. In some embodiments, contact surface 806 is circular. Contact surface 806 can be disposed on an end of main body 814. Main body 814 can have a cylindrical shape. Main body 814 can have a shape, including a shape defined by the outer perimeter of contact surface 806.

Main body 814 can have arms 808, 810. Arms 808, 810 can extend in a direction that is opposite the contact surface 806. Arms 808, 810 can each have a profile with curves. Arms 808, 810 can define a receiving region 812. Arms 808, 810 can deflect such that tube 204 can be positioned in the receiving region 812 with a press fit. In some embodiments, receiving region 812 can be sized to receive tube 204. In some embodiments, an insert can be placed in the receiving region 812 to allow the receiving region 812 to accommodate tubes 204 of varying sizes. Arm 808 can have a contact curve 816. Arm 810 can have a contact curve 818. Contact curve 816 can be positioned opposite contact curve 818. The offset distance between contact curve 816 and contact curve 818 can cause the arms 808, 810 to deflect when tube 204 is pushed against them to either place or remove the tube 204 from the receiving region 812. The offset distance between contact curve 816 and contact curve 818 can cause the arms 808, 810 to retain tube 204 once tube 204 is positioned within the receiving region 812.

Example Magnetic Clip Assembly

FIG. 9 depicts an example magnetic clip assembly 900. Magnetic clip assembly 900 can have a snap-fit device 1000 and a clip 1100. The snap-fit device 1000 can couple to the mating member 700. The clip 1100 can clip onto an item of clothing of a user, such as a belt. In some embodiments, the magnetic clip assembly 900 is one component.

FIGS. 10A-10B depict an example snap-fit device 1000. Snap-fit device 1000 can have an outer perimeter 1002. Outer perimeter 1002 can be any shape. In some embodiments, outer perimeter 1002 can be a circle.

Snap-fit device 1000 can have an extrusion 1016 that is offset from the edge defining the outer perimeter 1002. In some embodiments, a curve 1018 defines the transition from the outer perimeter 1002 to the extrusion 1016. In some embodiments, the extrusion 1016 has a flat surface. Extrusion 1016 can be any shape, which can include a circle or part of a circle.

Snap-fit device 1000 can have a receiving region 1004 that is defined, or at least partially defined, by extrusion 1016. Receiving region 1004 can be circular. Receiving region 1004 can have a flat surface. Receiving region 1004 can be connected to a channel 1012. Channel 1012 can extend from the receiving region 1004 to the outer perimeter 1002 such that the mating male clip assembly 600 can slide free from the receiving region 1004 via the channel 1012 and guided by alignment notches 1003. The receiving region 1004 and channel 1012 can define a recess with a perimeter that is defined by a semicircle and two straight line segments extending from two ends of the semicircle such that the line segments are parallel. The receiving region 1004 can be magnetic and/or have magnetic properties such that a male clip assembly 600 made of, at least in part, a ferrous metal is magnetically pulled toward the receiving region 1004 and/or retained at the receiving region 1004 after mating.

Snap-fit device 1000 can have a spring-loaded fastener 1001, also referred to as a mechanical snap feature and/or mechanical snap mechanism. Spring-loaded fastener 1001 can be positioned around the perimeter of the receiving region 1004. Spring-loaded fastener 1001 can be favorably positioned such that spring loaded fastener 1001 protrudes over part of the receiving region 1004. In some embodiments, spring-loaded fastener 1001 has plurality of fastener portions, which can include fastener portions 1006, 1008, and 1010. In some embodiments, fastener portions 1006, 1008, and 1010 are favorably positioned such that fastener portions 1006, 1008, and 1010 extend over receiving region 1004. Spring-loaded fastener 1001 can have a u-shaped inside perimeter. Spring-loaded fastener 1001 can have a circular or partially circular shaped inside perimeter. Spring-loaded fastener 1001 can be partially covered by and/or embedded in extrusion 1016 such that only portions of the spring-loaded fastener 1001 extend outside the extrusion 1016, which can include fastener portions 1006, 1008, and 1010.

The contact portions of the spring-loaded fastener 1001, which can include fasteners 1006, 1008, and 1010, can include beveled edges that assist the elastic deformation of the spring-loaded fastener 1001 as the male clip assembly 600 is inserted into the receiving region 1004. In some embodiments, the bevel 708 interfaces with the beveled edges of the contact portions of spring-loaded fastener 1001 as the male clip assembly 600 is inserted into the receiving region 1004. After the male clip assembly 600 is inserted into the receiving region 1004, the contact portions of the spring-loaded fastener 1001 can snap to interface with the retaining surface 711 and recess surface 712 of the mating member 700 of the male clip assembly 600. This can restrict the male clip assembly 700 to only decouple from the receiving region if slide in the direction of the channel 1012. Moving the male clip assembly 700 in the direction of the channel can cause fasteners 1006, 1008 to deflect away from each other, allowing the male clip assembly 700 to decouple from the magnetic clip assembly 900. Once the male clip assembly 700 is removed from the receiving region and no longer in contact with the fasteners 1006, 1008, the spring-loaded fastener 1001 can return to its natural state, which can include favorably extending over the receiving region 1004.

In some embodiments, the magnetic attraction of the receiving region 1004 and/or the spring-loaded fastener 1001 secure the male clip assembly 600 to the magnetic clip assembly 900, securing the stethoscope 200 to the magnetic clip assembly 900.

In some embodiments, this configuration can restrict coupling the male clip assembly 600 to the magnetic clip assembly 900 to two techniques. First, the male clip assembly 600 can be inserted by approaching the receiving region 1004 from a direction that is perpendicular to the flat surface of the receiving region 1004. This can also be described as approaching the receiving region 1004 while aligned with the axis defined by a circular shape of the receiving region 1004. Second, the male clip assembly 600 can be inserted by approaching the receiving region 1004 from the channel 1012. In some embodiments, this configuration can restrict removal of the mail clip assembly 600 to decoupling in the direction of the channel 1012, because the spring-loaded fastener 1001 and/or extrusion 1016 prevents pulling away in another direction.

In some embodiments, this configuration can allow a user to couple the male clip assembly 600 to the magnetic clip assembly 900 with one hand. In some embodiments, this configuration can allow a user to couple the male clip assembly 600 to the magnetic clip assembly 900 without looking down because the snap-fit device 1000 guides the male clip assembly 600 into the receiving region 1004 using the channel 1012, magnetic properties of the receiving region 1004, and/or the spring-loaded fastener 1001.

In some embodiments, the spring-loaded fastener 1001 and/or magnetic properties of the receiving region 1004 prevent the stethoscope 200 and male clip assembly 600 from being dislodged during routine activity. In some embodiments, the male clip assembly 600 may only be decoupled form the snap-fit device 1000 by moving the male clip assembly 600 in an upward direction.

Figure 11A:
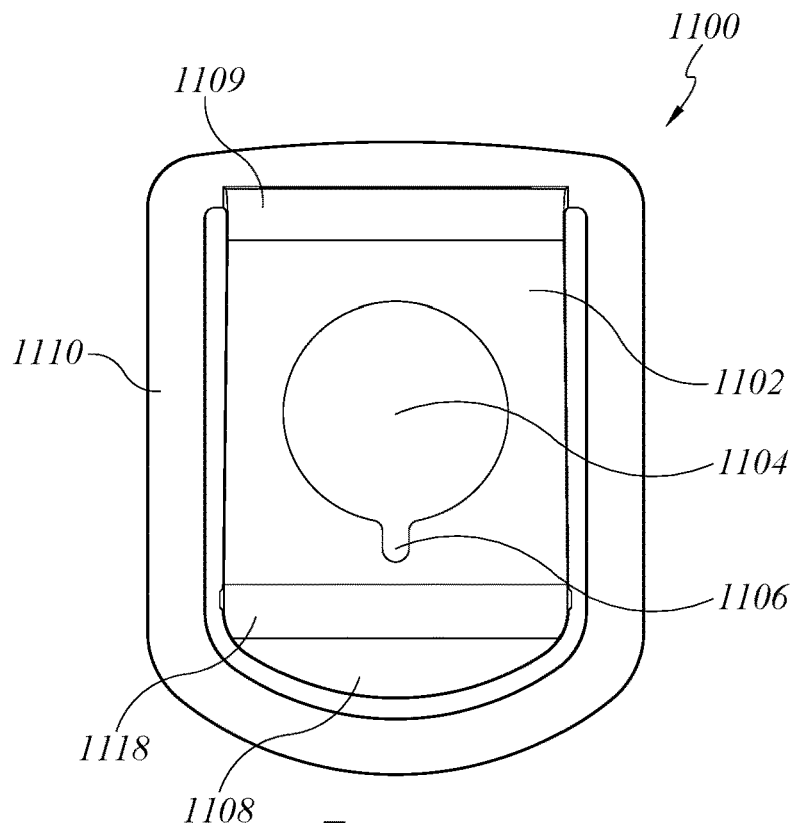
FIG. 11A is an illustrative example of a front view of a clip.
Figure 11B:
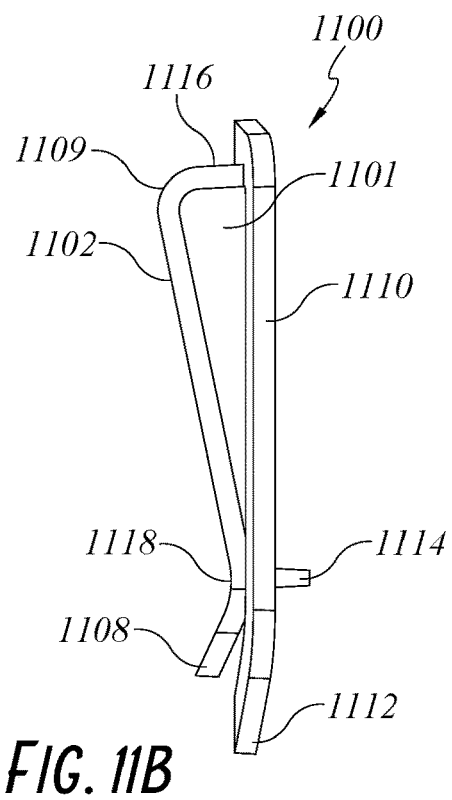
FIG. 11B is an illustrative example of a side view of a clip.
Figure 11C:
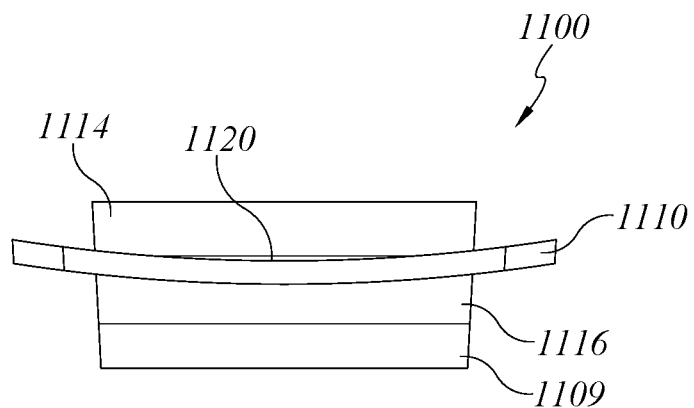
FIG. 11C is an illustrative example of a top view of a clip.
Figure 11D:
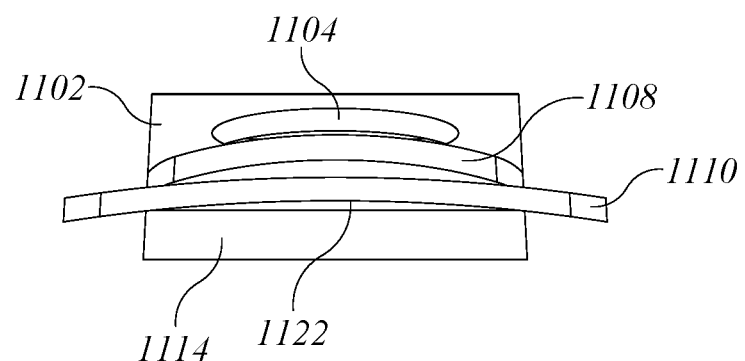
FIG. 11D is an illustrative example of a bottom view of a clip.

A side of the snap-fit device 1000, opposite the side with the receiving region 1004, can have a threaded connector 1022. Threaded connector 1022 can be configured to be inserted into aperture 1104 of clip 1100, described in references to FIGS. 11A-11B. A retaining ring 1020 can be configured to screw onto the threaded connector 1022. Retaining ring 1020 can have an inner perimeter that is threaded. Retaining ring 1020 can have an outer perimeter that is the same as the outer perimeter 1022. The snap-fit device 1000 can be coupled to the clip 1100 by inserting the threaded connector 1022 into the aperture 1104 of clip 1100 and then screwing the retaining ring 1020 onto the threaded connector 1022.

FIGS. 11A-11D depict an example clip 1100. Clip 1100 can have a panel 1102. Panel 1102 can have an aperture 1104. Aperture 1104 can be configured to receive a threaded connector 1022. Aperture 1104 can be circular. Aperture 1104 can have an alignment portion 1106. Alignment portion 1106 can interface with an alignment member disposed on the snap-fit device 1102 such that the clip 1100 and snap-fit device are correctly oriented. In some embodiments, the alignment portion 1106 and alignment member ensure that the channel 1012 is oriented vertically.

Clip 1100 can have a frame 1110. The frame 1110 can have an inner perimeter that is larger than the perimeter of the panel 1102. The frame 1110 can be connected to the panel 1102 via a transverse portion 1116 that extends transversely away from the frame 1110 and is connected to the panel 1102 via curve 1109. The panel 1102 can be oriented at an angle to the frame 1110. This configuration can define a channel 1101 and/or gap that can receive a portion of a user's item of clothing, such as a belt, waistband, and/or portion of a pocket.

The panel 1102 can have a grasping portion 1108 disposed on a side of the panel 1102 opposite the curve 1109. The grasping portion 1108 can be joined to the panel 1102 via a curve 1118, which can curve such that the grasping portion 1108 extends away from the frame 1110. The grasping portion 1108 can be grasped, or otherwise manipulated, by a user to cause the panel 1102 to elastically deflect between different positions.

A end portion 1112 of the frame 1110 can be oriented such that end portion 1112 extends away from the proximate portions of frame 1110 at an angle. The end portion 1112 can extend in a direction that is generally the same as the extension direction of the grasping portion 1108. End portion 1112 can have a curve 1122. Curve 1122 can facilitate a fitted contact between the frame 1110 and the user and/or user's item of clothing. The end of frame 1110 opposite end portion 1112 can have a curve 1120. Curve 1120 can have the same radius as curve 1122. Curve 1120 can facilitate a fitted contact between the frame 1110 and the user and/or user's item of clothing.

A retaining member 1114 can be positioned on a side of the panel 1102 closest to the frame 1110. Retaining member 1114 can be positioned on curve 1118. Retaining member 1114 can extend in the direction of the frame 1110. In some embodiments, the panel 1102 is favorably positioned such that the retaining member 1114 extends beyond a plane defined by the frame 1110. Retaining member 1114 can have varying lengths and/or cross-sections. Retaining member 1114 can have a cross-section that is larger at an end that couples to panel 1102 and smaller at an end that extends away from panel 1102. Retaining member 1114 can be configured to secure clip 1110 onto an item of clothing of a user, such as a belt. In some embodiments, clip 1000 does not have a retaining member 1114.

A user can couple magnetic clip assembly 900 onto an item of clothing, such as a belt waistband, and/or pocket, by inserting the end portion 1112 of the frame 1110 between the belt of a user and the user's body. The user can grasp, or otherwise move, the grasping portion 1108 such that the panel 1102 deflects away from the frame 1110 that is secured by the belt of a user. The user can push the magnetic clip assembly 900 such that the belt is disposed in the channel 1101 between the panel 1102 and the frame 1110. The user can release the grasping portion 1108 allowing the panel 1102 to deflect back to its natural state and pinch the belt between the panel 1102 and the frame 1110.

In some embodiments, a user can align channel 1101 with an item of clothing and push clip 1100 into position such that the item of clothing is disposed in the channel 1101.

In some embodiments, a user can remove the magnetic clip assembly 900 from an item of clothing of the user with the remainder of the stethoscope carrying system 100 and the stethoscope 200 coupled together. This configuration can allow removal of the stethoscope carrying system 100 and stethoscope 200 altogether. In some embodiments, a user can clip the magnetic clip assembly 900 to an item of clothing while the stethoscope carrying system 100 and stethoscope 200 are coupled together. This can help a user to easily attach or detach the stethoscope carrying system 100 and stethoscope 200.

The components of the stethoscope carrying system 100 can be made of varying materials, such as metals, metal alloys, polymers, ceramics, or any other suitable material.

Terminology

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for carrying a stethoscope, the system comprising:
    a magnetic clip assembly, the magnetic clip assembly comprising a snap-fit device and a clip,
        the snap-fit device comprising a magnetic receiving region and a locking mechanism, the locking mechanism disposed around a perimeter of the magnetic receiving region and comprising spring-loaded fasteners, and
        the clip configured to couple to the snap-fit device and releasably couple to an item of clothing of a user; and
    a male clip, the male clip configured to releasably couple to a tube of the stethoscope and to mate with the magnetic receiving region of the snap-fit device and engage with the spring-loaded fasteners of the locking mechanism.

2. The system of claim 1, wherein the snap-fit device comprises a recess.

3. The system of claim 2, wherein the magnetic receiving region comprises a circular shape disposed on a surface within a perimeter defined by the recess.

4. The system of claim 2, wherein an internal perimeter of the recess is defined by a circular shape and a channel.

5. The system of claim 1, wherein the spring-loaded fasteners are biased inward such that the spring-loaded fasteners extend over the magnetic receiving region.

6. The system of claim 1, wherein the spring-loaded fasteners are configured to deflect to accommodate insertion of the male clip into the magnetic receiving region and to lock the male clip in the magnetic receiving region after insertion therein such that the male clip is configured to only be removed from the magnetic receiving region via sliding in a given direction.

7. The system of claim 1, wherein the male clip is configured to only be inserted within the magnetic receiving region by approaching the magnetic receiving region from a direction perpendicular to a surface of the magnetic receiving region.

8. The system of claim 1, wherein the male clip is configured to only be removed from the magnetic receiving region by sliding the male clip through a channel connected to the magnetic receiving region.

9. The system of claim 1, wherein the male clip is configured to couple to the tube of the stethoscope such that the male clip is positioned 2.5-5.5 inches away from a headpiece of the stethoscope.

10. The system of claim 1, further comprising a chestpiece-securing assembly, the chestpiece-securing assembly comprising:
a groove piece that is configured to releasably couple to the tube of the stethoscope; and
a back piece configured to releasably couple to the groove piece such that a fork region of the stethoscope is disposed between the groove piece and the back piece;
wherein the groove piece is configured to position a headpiece of the stethoscope between binaural arms of the stethoscope, arranging the stethoscope in a folded position, when the groove piece is coupled to the tube of the stethoscope and the back piece.

11. The system of claim 10, wherein the groove piece comprises a groove defining a receiving region that couples to the tube of the stethoscope with a press fit.

12. The system of claim 10, wherein the groove piece comprises a plurality of support arms with a hook disposed on an end of each of the plurality of support arms, wherein the back piece comprises a plurality of apertures configured to releasably couple to the hook disposed on each of the plurality of support arms.

13. The system of claim 12, wherein the hook of each of the plurality of support arms of the groove piece are configured to be releasably coupled to a surface proximate each of the plurality of apertures of the back piece with a snap fit.

14. The system of claim 1, wherein the clip of the magnetic clip assembly is configured to be clipped onto an item of clothing of the user.

15. The system of claim 1, wherein the male clip comprises two arms that are configured to deflect around the tube of the stethoscope.

16. The system of claim 1, wherein the male clip comprises a ferrous metal.

17. A system for carrying a stethoscope, the system comprising:
a clip assembly, the clip assembly comprising a magnetic receiving region, a locking mechanism, and a clip,
the locking mechanism disposed proximate to the magnetic receiving region and comprising spring-loaded fasteners, and
the clip configured to couple the clip assembly to an item of clothing; and
a male clip, the male clip configured to releasably couple to a tube of the stethoscope, to make contact with the magnetic receiving region, and to interface with the spring-loaded fasteners of the locking mechanism.

18. The system of claim 17, further comprising a chestpiece-securing device, the chestpiece-securing device configured to be coupled to a fork region of the stethoscope and to releasably couple to the tube of the stethoscope such that a headpiece of the stethoscope is positioned between binaural arms of the stethoscope.

19. A system for carrying a stethoscope, the system comprising:
a magnetic clip, wherein the magnetic clip comprises a magnetic receiving region, mechanical fasteners, and a clasp,
the mechanical fasteners positioned proximate a perimeter of the magnetic receiving region, and
the clasp is configured to couple the magnetic clip to an item of clothing; and
a male clip, the male clip configured to releasably couple to a tube of the stethoscope, magnetically couple to the magnetic receiving region, and engage with the mechanical fasteners.

20. The system of claim 19, further comprising a chestpiece-securing device, the chestpiece-securing device configured to be coupled to a fork region of the stethoscope and to releasably couple to the tube of the stethoscope such that the stethoscope is in a folded position.

* * * * *